(12) United States Patent
Gertzman et al.

(10) Patent No.: US 6,506,192 B1
(45) Date of Patent: Jan. 14, 2003

(54) ALLOGRAFT BONE FIXATION SCREW

(75) Inventors: Arthur A. Gertzman, Stony Point, NY (US); Raymond G. Ferrara, Jr., Branchburg, NJ (US); Timothy G. Haines, Minneapolis, MN (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 110 days.

(21) Appl. No.: 09/585,412

(22) Filed: Jun. 2, 2000

Related U.S. Application Data

(63) Continuation-in-part of application No. 09/275,024, filed on Mar. 24, 1999, now Pat. No. 6,099,529, and a continuation-in-part of application No. 09/178,684, filed on Oct. 26, 1998, now Pat. No. 6,162,225.

(51) Int. Cl.⁷ .............................................. A61B 17/86
(52) U.S. Cl. .......................................... 606/73; 606/77
(58) Field of Search .............................. 606/72, 73, 65, 606/66, 232; 411/500–510, 399, 401, 400, 409, 1, 2, 402

(56) References Cited

U.S. PATENT DOCUMENTS

| | | |
|---|---|---|
| 172,351 A | 1/1876 | Sloan |
| 173,356 A | 2/1876 | Sloan |
| 374,701 A * | 12/1887 | Quinby |
| 755,804 A | 3/1904 | Smith |
| 1,300,275 A | 4/1919 | Johnson |
| 1,336,794 A | 4/1920 | Stepanian |
| 2,049,105 A * | 7/1936 | Clarke |
| 4,463,753 A | 8/1984 | Gustilo |
| 4,724,731 A | 2/1988 | Onofrio |
| 4,823,650 A | 4/1989 | Tuttle |
| 5,012,624 A | 5/1991 | Dahlgren |
| 5,367,926 A | 11/1994 | Mikic et al. |
| 5,403,136 A | 4/1995 | Mathys |
| 5,443,482 A | 8/1995 | Stone et al. |
| 5,730,744 A | 3/1998 | Justin et al. |
| 5,868,749 A * | 2/1999 | Reed ............................. 606/76 |
| 5,968,047 A | 10/1999 | Reed |

OTHER PUBLICATIONS

F. Albee, *Bone Graft Survey in Disease, Injury and Deformity*, p. 22 (1940).

F. Albee, *The Improved Albee Bone Mill*, American Journal of Surgery, p. 657 (Mar., 1938).

* cited by examiner

*Primary Examiner*—David O. Reip
(74) *Attorney, Agent, or Firm*—John S. Hale; Gipple & Hale

(57) ABSTRACT

A sterile allograft bone screw comprising a screw shank with a uniform diameter threaded portion, an unthreaded portion with a outwardly tapered conical portion and a rectangularly shaped driving head portion with substantially wedge shaped end which can be engagably seated in a seat of a driver member.

16 Claims, 4 Drawing Sheets

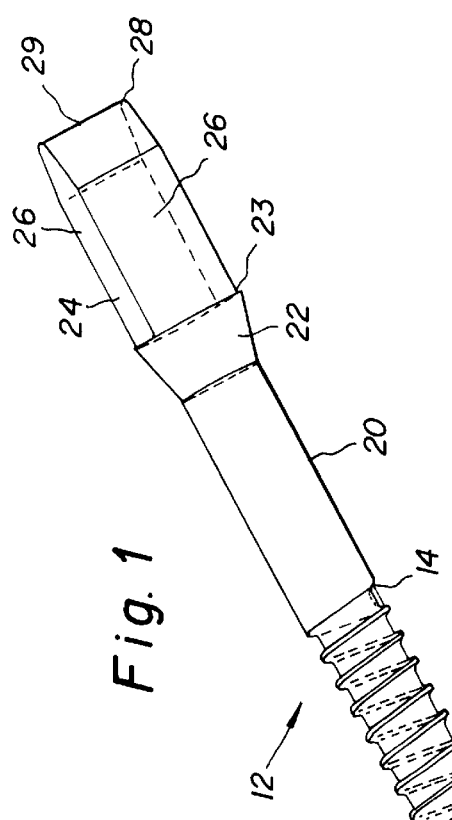
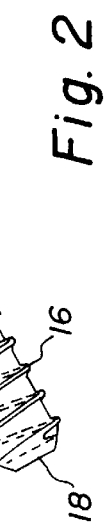
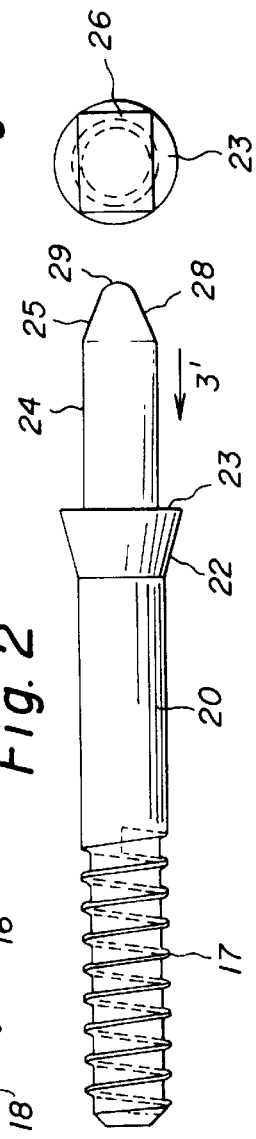
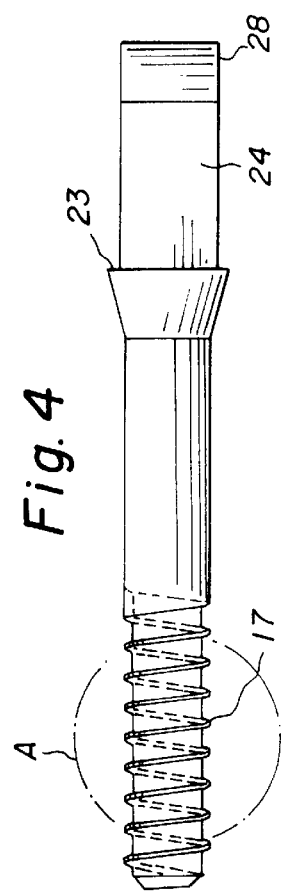

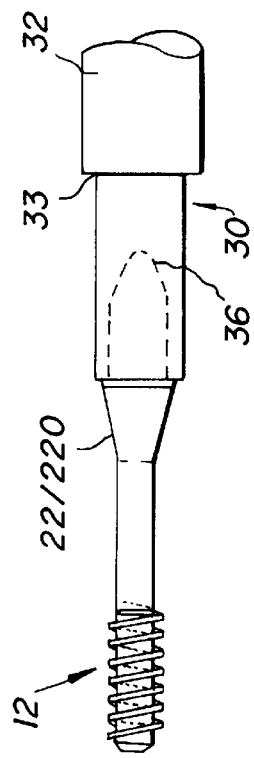
Fig. 8
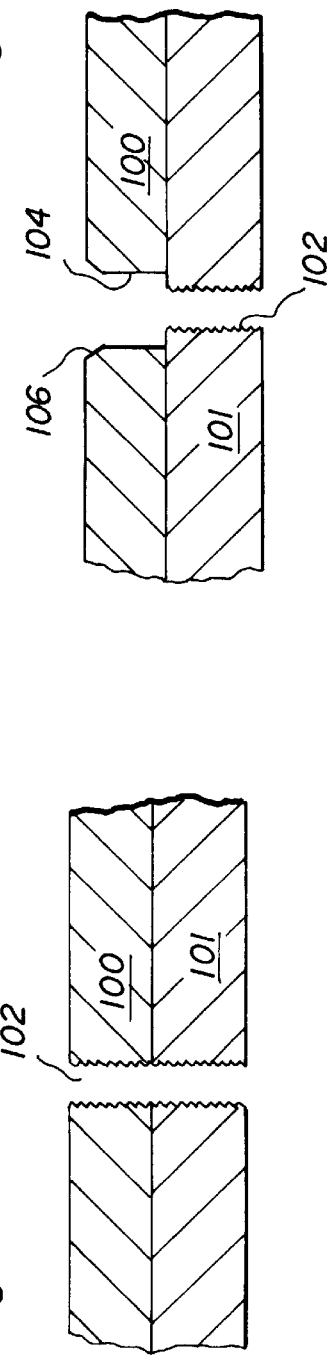
Fig. 10
Fig. 9
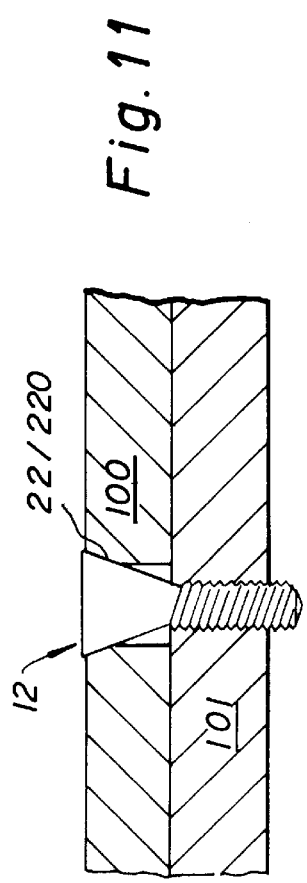
Fig. 11

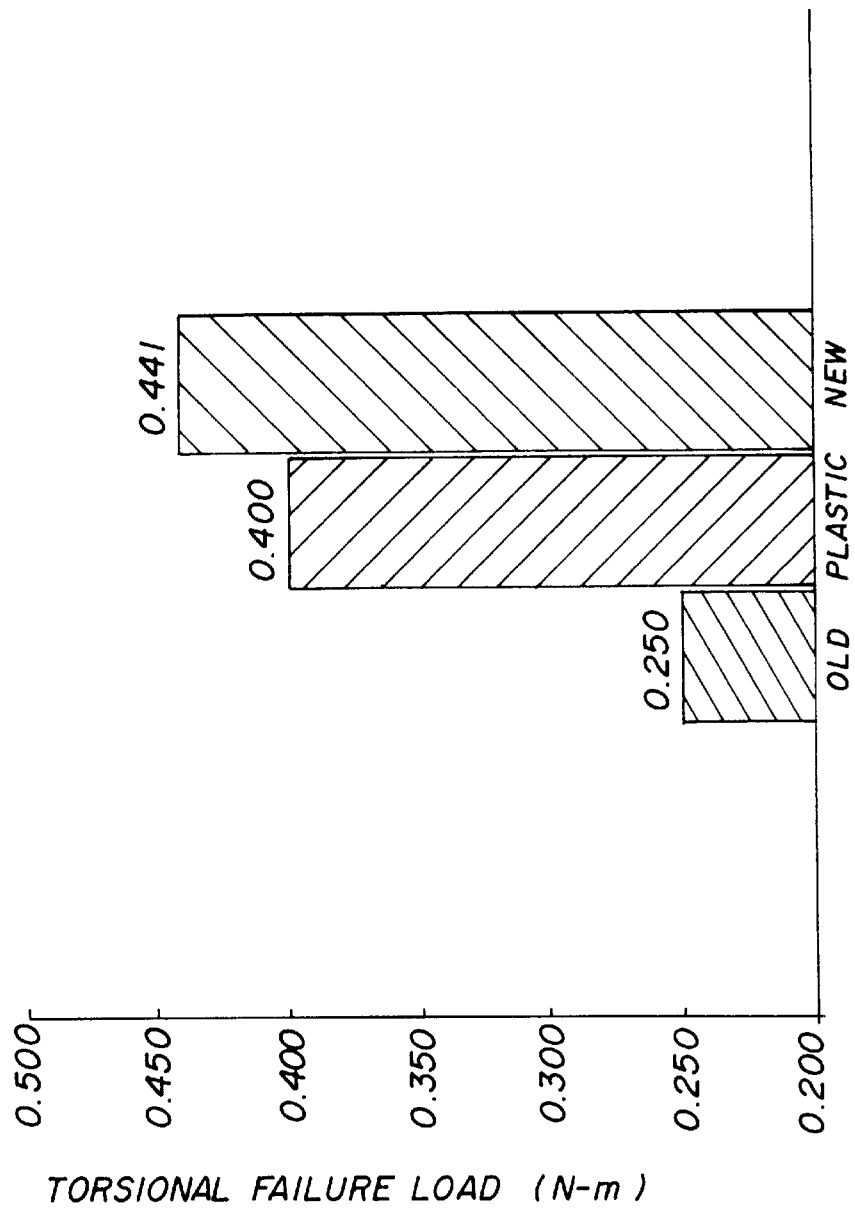

ALLOGRAFT BONE FIXATION SCREW

RELATED APPLICATIONS

This application is a continuation-in-part of application Ser. No. 09/178,684, filed Oct. 26, 1998, now U.S Pat. No. 6,162,225, and application Ser. No. 09/275,024, filed Mar. 24, 1999, now U.S. Pat. No. 6,099,529.

BACKGROUND OF THE INVENTION

1. Field of Invention

The present invention generally relates to threaded devices used to facilitate bone fracture or osteotomy fixation in human surgery and more specifically relates to threaded devices made of allograft bone.

2. Description of the Prior Art

The prior art contains many references directed to fastener drivers which drive screws having a Phillips head, standard slot head or other heads having various shaped slots or recesses which receive the torque from the driver end. See for example the prior art shown in U.S. Pat. No. 5,367,926. There are other examples of prior art fastener drivers having female driver ends which receive and drive fasteners having a male torque receiving end. Typical driver screw fasteners and screws of such a construction are shown in U.S. Pat. Nos. 755,804; 1,300,275; 4,724,731; 5,012,624; 5,443,482 and 5,730,744. Wrenches having a female driving end which drive caps or nuts are shown by U.S. Pat. Nos. 1,336,794 and 4,823,650.

Several patents such as U.S. Pat. Nos. 172,351 and 173,356 show screws having a head formed with a wedge shaped groove or slot which receives the angular notch of a driver head to transmit torque and drive the screw. While most screws have a uniform diameter shank, U.S. Pat. Nos. 4,463,753 and 5,403,136 disclose bone screws which have a tapered shank which cause compression of the bone between the distal end of the screw and the taper.

Millions of people suffer from a variety of musculoskeletal disorders or traumatic occurrences necessitating the use of devices to reduce osteotomies or fractures. Many different means have been developed to facilitate fixation and healing of the traumatized bone tissue. In the past, metallic pins and screws have been used to establish initial mechanical stability of the trauma site, and to facilitate permanent, mechanically stabile fracture or osteotomy healing.

The most significant difficulties with screws and pins currently used to facilitate fixation include the residual presence of "hardware" that may migrate, include adverse tissue reaction to the presence of foreign particulate debris, and otherwise compromise the functionality of the fixation. Some recently offered products feature bioresorbable material technology which allows for gradual absorption of the screws and pins. Unfortunately, these materials may fall short of expected performance due to incomplete osseointegration of patient bone. Allograft bone offers a suitably strong, biocompatible, and bioresorbable material that addresses these deficiencies.

Screws made completely of allograft bone have been described in F. Albee, *Bone Graft Surgery in Disease, Injury and Deformity* p. 22 (1940); and F. Albee, *The Improved Albee Bone Mill*, American Journal of Surgery p. 657 (March 1938). These screws offer the advantage of the biointegration of allograft bone tissue. However, the conventional slotted or rectangular head designs commonly used in metal screws when used with allograft bone screws, result in premature failure of the screws during intraoperative insertion due to excessively high shear forces applied to the head and the transition between the head and threaded portion of the screw. This shearing is due to several factors. First, and foremost, while bone is quite strong in compressive loading, it is relatively weak in tension and shear. Since the torque applied to a screw induces shear stresses, the design of a screw made of allograft bone tissue must be as robust as necessary with respect to torque loading.

Additional screws and fasteners of various construction which have been made of allograft bone are additionally shown in U.S. Pat. No. 5,968,047.

There are several problems with screws presently used in the prior art. As can be appreciated, the screws are small with a round or cylindrical head and are difficult to place in the driver or area to be fastened because of the nature of the surgery, namely that the same are used in circumstances where fluid such as blood is present, thus, presenting a slippery condition for handling and use.

In addition, the use of a cylindrical barrel or round head on the screw is not the most efficient way of transmitting torque to the screw when the same is screwed into the bone and the present invention allows a maximum torque to be applied over the driver head portion of the screw allowing the same to be more easily inserted.

SUMMARY OF THE INVENTION

In response to the needs still left unresolved by the prior art devices, the present invention contemplates allograft bone screws made of cortical and cancellous bone with both a unique head design and a bone formation treatment which solves the deficiencies of the prior art prostheses.

The inventive screw design offers two unique features which fulfill the potential of allograft bone as an ideal material for screws used in fracture and osteotomy reduction. The first unique feature is a drive head having a rectangular shaped body with a wedge end which mates with a specialized driver used to apply torque to the screw. The second unique feature is an outwardly tapering shank portion adjacent the rectangular shaped body which provides an undercut for the head providing a tight engagement of the screw in the bone bore. This drive head accomplishes two desirable functions. The first function is that it avoids localized tensile stresses inherent in standard drive designs that would lead to mechanical failure of an allograft bone screw and the second function is the ability of this body to place an increased torque on the screw thread that also avoids mechanical failure of the screw.

It is an object of the invention to provide a flat surface abutting the drive head allowing the tapered section of the screw to be easily cut flush along the bore surface.

Thus the present screw design is both easy to use and offers the ideal physiological response of patient tissue to allograft bone tissue.

In the operation of the invention, a method is provided for implanting a bone screw into two separate bone sections. The approach includes the steps of drilling a first tapped bore drill through both pieces of bone. The first bone piece bore is then overdrilled to a larger diameter and countersunk. The bone screw head is then mounted in a rectangular or square chamber having a rear V shaped notch formed in the driver head. The bone screw is then driven or screwed into the prepared bone bore until the undercut of the bone screw engages the countersink. The rectangular portion of the bone screw extending outward past the surface of the outer bone piece is then cut off so that the head of the bone screw is flush with the fastened bone piece surface.

These and other objects, advantages, and novel features of the present invention will become apparent when considered with the teachings contained in the detailed disclosure along with the accompanying drawings.

BRIEF DESCRIPTION OF THE DRAWINGS

FIG. 1 is a perspective view of the inventive bone fixation screw with portions shown phantom;

FIG. 2 is a top plan view of the bone fixation screw shown in FIG. 1;

FIG. 3 is an end view of FIG. 2 viewed along the arrow 3';

FIG. 4 is a side elevational view of the bone fixation screw shown in FIG. 1;

FIG. 8 is a side assembled exploded view partially in phantom of the bone fixation screw and driver assembly;

FIG. 9 is a schematic view of two adjacent bone pieces being drilled with a tapped bore;

FIG. 10 is a schematic view of the bone pieces shown in FIG. 9 with the first bone piece being overdrilled with a greater diameter bore and a countersink;

FIG. 11 is a schematic view of the bone pieces shown in FIG. 10 with the bone fixation screw mounted in the bone pieces and the screw head severed flush to the bone surface; and FIG. 12 is a graph showing comparative screw torsional failure loads of the inventive, screw compared with other prior art screws;

DETAILED DESCRIPTION OF PREFERRED EMBODIMENT

The preferred embodiment and the best mode of the present invention is shown in FIGS. 1 through 5.

It is an accepted fact that the initiation of mechanical failure in a material occurs at the outer surface of the material. Also, it is recognized that rapid changes in cross sectional geometry act as localized "stress risers", significantly increasing the risk of failure under load. The present inventive bone screw 12 solves these problems particularly when the screw is constructed of allograft bone. The preferred material of the bone screw is cortical allograft bone.

Figure 5:
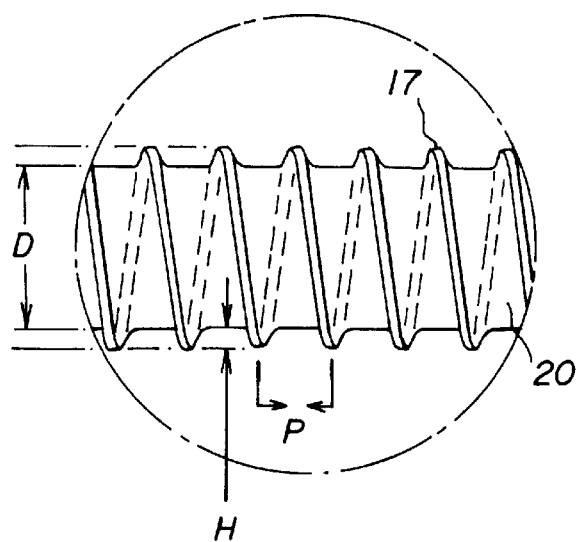
FIG. 5 is an enlarged partial elevational view of the threads of the bone fixation screw shown in Circle A of FIG. 4.
Figure 6:
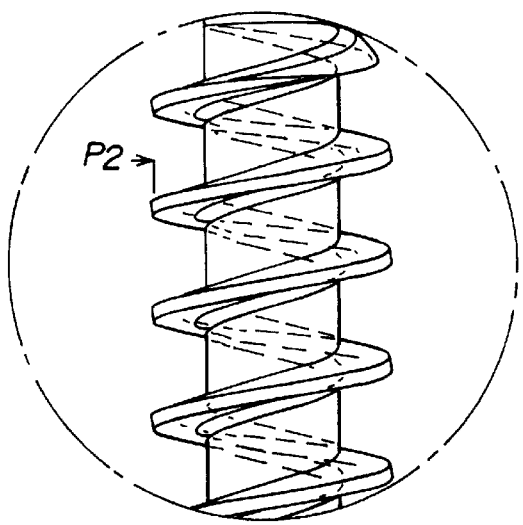
FIG. 6 is an enlarged partial elevational view of another thread embodiment configuration which can be used in a cancellous bone fixation screw.

The bone fixation screw 12 has a shark 14 with a threaded portion 16 ending in a distal tip 18 and an unthreaded portion 20 which has a section 22 is tapered outward to form a frustrum conical configuration with a flat end portion 23 from which a drive head 24 extends. The flat end portion preferably has a 4.0 mm or −0.1 mm diameter with the sides of the drive head ranging from 3.0 mm to 4.0 mm in width. The drive head 24 has a rectangular shaped body with planar side surfaces 26 and a wedge end 28. The end 29 of the wedge 28 is rounded. The tapered section 22 of the shank 14 is preferably tapered to form an angle ranging from about 30° to about 40° with the central axis of the shank. The bone screw 12 shown in FIGS. 1 through 4 preferably has a taper or undercut angle of about 30° while a bone screw used on cancellous bone with the thread shown in FIG. 6 preferably has a taper or undercut angle of about 40°. The overall length of the bone screw 12 ranges from 27 mm to 49 mm with the shank ranging from 18 mm to 40 mm. As noted the screw can have overall lengths of 27, 29, 31, 33, 35, 49 mm + or −1.0 mm with the shank length being respectively 18, 20, 22, 24, 26 and 40 mm + or −0.5 mm. As shown in FIG. 5 the shank has a 2.8 mm diameter D with a screw thread height H from shank to crest of 0.35 mm. When the shank is used on cancellous bone it will have at least a 4.0 mm diameter. The screw pitch P of the cortical bone screw is approximately 1.25 mm and the screw pitch P2 of the cancellous screw thread is approximately 1.75 mm. The bevel of the thread is preferably about 60°. However the included angle at the thread root can vary from 10° to 80°. It will be appreciated that while these dimensions are preferred dimensions that the same may be varied while retaining the structure and function of the invention without limiting same. The threaded portion 16 preferably is formed with a single helical thread 17 formed on the exterior surface of the shank to engage the bone material 100 and draw the screw 12 down into the bore 102. As shown in FIGS. 1–4 the thread runs along the shank about ½ the length of the shank. The thread 17 can be a #6-32 UNC, a #6-40 UNS or BA4 (British Aircraft) thread. UNC and UNS threads have a helical generally V-shaped thread with a 60° bevel. Other screw threads which can be used are standard screw threads (ANSI): #0, #1, #2, #3, #4, #5, #6, #8, #10, #12 and ¼ inch, ⁵⁄₁₆ inch and ⅜ inch. Metric threads M 1.6, M 2, M 2.5, M 3, M 4, M 5, M 6, M 8 and M 10 can also be used. It is also contemplated that the threaded portion 16 may include a self-tapping thread having grooves extruded along the longitudinal axis of the threads providing sharp leading edges and space for removal of osseous debris. The self-tapping aspect of the threaded portion facilitates insertion and anchoring of the screw into a patient's bone. The drive head 24 has a rectangular body which may be square or rectangular in cross section with a wedge shaped end 28 which may be rounded at its end 29 as shown in FIG. 2.

Figure 7:
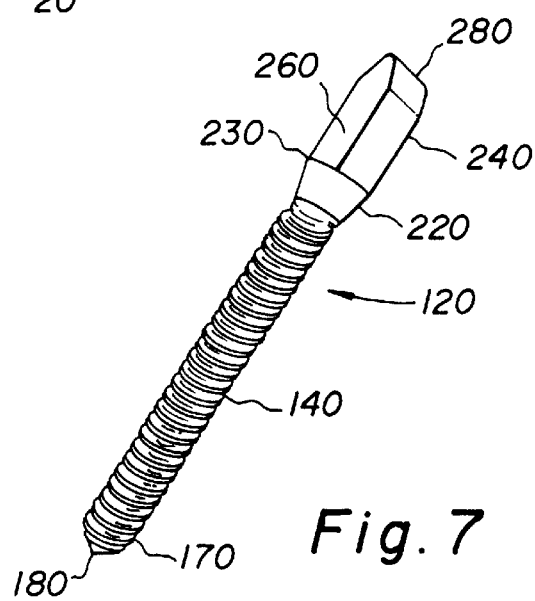
FIG. 7 is a perspective view of another embodiment of the inventive bone fixation screw having a thread along the shank length.

Another embodiment of the bone fixation screw is shown in FIG. 7. The bone fixation screw 120 has a substantially fully threaded shank 140 ending in a distal tip 180 at one end and an unthreaded outwardly tapered portion 220 ending in a drive head 240 with a rectangular body 260 and wedge end 280. The tapered portion 220 of the shank 140 is preferably tapered with the cross section forming an angle ranging from 30° to 40°. The overall length of the screw is preferably about 49 mm and the threaded shank has a length of about 33 mm with a 2.8 mm diameter and a thread height of 0.35 mm. The head 240 has a rectangular body 260 has a preferred length of about 9 mm with a wedge shaped tip 280. The pitch of the screw threads is approximately 1.25 mm and the bevel of the thread is preferably about 60°. However the included angle at the thread root can vary from 10° to 80°. It will be appreciated that these dimensions are preferred dimensions and may be varied while retaining the structure and function of the invention without limiting same. The threaded portion is formed with a single helical thread 170 formed on the exterior surface of the shank to engage the bone material 100/101 and draw the screw 120 down into the bore 102. The thread 170 can be a #6-32 UNC, a #6-40 UNS or BA4 (British Aircraft) thread. UNC and UNS threads have a helical generally V-shaped thread with a 60° bevel. Other screw threads which can be used are standard screw threads (ANSI): #0, #1, #2, #3, #4, #5, #6, #8, #10, #12 and ¼ inch, ⁵⁄₁₆ inch and ⅜ inch. Metric threads M 1.6, M 2, M 2.5, M 3, M 4, M 5, M 6, M 8 and M 10 can also be used. It is also contemplated that the threaded portion may include a self-tapping thread having grooves extruded along the longitudinal axis of the threads providing sharp leading edges and space for removal of osseous debris. The self-tapping aspect of the threaded portion facilitates insertion and anchoring of the screw into a patient's bone.

All of the bone screws 12/120 described above can be coated with a bone morphogenic protein or treated to absorb a bone morphogenic protein to speed up bone growth and absorption into bone.

The rectangular drive geometry of the head also acts as a torque maximizer due to the ability of the driver 30 engage the planar walls of the rectangular body until a desirable torque limit is reached.

As can be seen from the graph shown in FIG. 12, the present invention has a significantly higher torsional failure load (requires more torque to shear the screw) than that of a previous cylindrical screw used by the present assignee and a widely used surgical absorbable plastic screw marketed by Bionx under the trademark SMARTSCREW. Testing was conducted on thirty allograft bone screws using a materials testing machine. The screw design of the present invention was compared to the another cylindrical design of the assignee and the Bionx SMARTSCREW. The present inventive design tested 12 screws consisting of 3 bone donors with 4 screws per donor of the inventive design, 18 screws consisting of 6 bone donors with 3 screws per donor of the older cylindrical drive head design and 9 Bionx SMARTSCREW absorbable screws. Each screw was inserted into a lower bone block until "snug" and then placed in the lower bone block holding fixture on a testing device. The insertion torque to the "snug" feeling was=0.1 N-m. The screw was turned with a custom driver and programmed to rotate at a rate of 0.1 degree per second. After failure, the program was stopped and the failure load, in Newton-Meters, was recorded.

The 3.5 mm cylindrical drive head allograft screw with a 2.4 mm core diameter had a average failure load (N-m) 0.250 and the 3.5 mm Bionx screw had an average failure load (N-m) of 0.400. The present 3.5 mm allograft screw (2.8 mm core dia.) had an average failure load (N-m) of 0.441. It can thus be seen that the present inventive screw performed better in the torque tests then the other comparative bone screws.

The inclined planes 25 of the drive head when extended to intersect form an angle which can range between 15° and 60° but preferably form a 45° angle.

One feature of all of the fixation screws is the tapered undercut 22/220 located between the rectangular body portion of the drive head 24/240 and the threaded portion 16/140 of the screw. This tapered undercut feature accomplishes two ends. First, it acts to provide a gradual change in cross sectional geometry thus increasing the strength of the component under load and second it provides a tight engagement of the screw in the bone bore. The rear end surface of the tapered section is flat and preferably perpendicular to the axis of shank and the planar side walls of the drive head body. This provides a shoulder or stop for the drive tool as well as to provide a clear surface for the cutting tool once the screw has been inserted so that the screw can be cut flush to the bone. In comparison to standard screw designs where the underside of the drive geometry sharply changes, the strength of the tapered undercut is far superior both under torque loading inherent in insertion and tensile loading post operatively as well as providing easy handling of the screw during surgery.

The tapered undercut also acts as a means of securing the screw within the bone wall 100 after the drive head 24/240 has been cut flush with the bone surface. The taper allows for two means of securing fixation across the fracture or osteotomy. First, the taper feature allows for compression across the fracture site as would a conventional screw design. However, the taper also acts as a "taper lock" similar to those found in femoral head/femoral lock neck mating geometry's in Total Hip Replacement implants ensuring that even under cyclic loading conditions the screw will not "back out" of the threaded bone thus releasing the tension across the fracture or osteotomy.

Both the rectangular shaped drive head 26/260 and the tapered undercut 22/220 serve to increase the strength of the respective screw 12/120 under torsion loading. Torsion loading induces tangential or planar shear stresses in planes normal to the longitudinal axis of the torque induced. The magnitude of these stresses is proportional to the cross section area of the material thus loaded.

The present invention as is shown in FIG. 12 provides an increase in torsional loading strength which is of great importance in allograft bone screws. The drive head 24/240 and tapered undercut 22/220 of the respective screw can also be formed of other biomaterial including, but not limited to, bioceramics, biocompatible/bioresorbable polymeric materials, biocompatible carbon fiber reinforced polymer and the multitude of orthopaedic inert implant metals including stainless steel, cobalt-chromium-molybdenum alloys, titanium and titanium alloys, tantalum and niobium and their alloys, HEDROCEL, a porous tantalum-carbon composite which has a modulus of elasticity that approximates that of human bone as well as other materials used in surgical applications.

An implant driver 30 is used to drive the screw 12/120. The cylindrical shaft body 32 of the driver is formed with a head 34 defining a rectangular chamber to receive the driving head of the screw. The head also 34 defines an angular "V" shaped notch or recess 36 at its distal end preferably of 45° or any other suitable angle which engages and seats the wedge shaped end of head 24/240 of the bone screw therein.

In seating the screw, a threaded bore 102 is drilled through both bone portions 100 and 101, with portion 100 being over drilled with a larger diameter bore 104 having a countersink 106 of a tapered geometry which widens from the diameter of the bore at the same angle as the tapered portion 22/220. The bore can be cut in a single stage or two stage operation in which the countersink is initially cut into the bone in the second cut or followed by a third cut. In the single stage cut, a drill (not shown) is provided with a drill bit with a widened tapered portion which enables drilling a bore with a tapered end section geometry which is of the same size and configuration as the undercut 22/220 of screw. A bone screw comprising a shank with a uniform diameter threaded portion, and a rectangular driving head 24/240 with a wedge shaped end is seated in the rectangular shaped notched seat 36 in the driver member head 34. The driver member is preferably constructed of steel and comprises a cylindrical shaft body 32 and a driver head 34 secured or integrally formed with the shaft body. The screw 12/120 is driven into the previously drilled stepped bore 102/104 until the tapered portion or countersink 106 of the bore creates a mating surface for the tapered undercut 22/220 of the bone screw. The rectangular portion of the head allows the driver head to be raised above the bone surface being repaired providing clearance for the driver. The head 24/240 is then cut off flush to the bone surface along the flat end surface 23/230 as is shown in FIG. 2.

In the foregoing description, the invention has been described with reference to a particular preferred embodiment, although it is to be understood that specific details shown are merely illustrative, and the invention may be carried out in other ways without departing from the true spirit and scope of the following claims:

What we claim is:

1. A bone screw constructed of a biomaterial selected from a group consisting of allograft bone, bioceramics, bioresorbable polymeric material, said bone screw comprising a cylindrical shank with a threaded portion and an unthreaded portion, one section of which tapers outwardly, said outwardly tapering section being adjacent to an integrally formed drive head to form a tapered undercut for the drive head, said drive head being formed with a rectangular shaped body defining a wedge shaped end, said tapered undercut being funnel shaped and tapered at an angle ranging from about 20° to 45° from the center axis of the cylindrical shank and has a flat end surface transverse the center axis of the cylindrical shank adjacent said drive head to form a shoulder.

2. A bone screw as claimed in claim 1 wherein said screw is threaded about ½ the length of its shank.

3. A bone screw as claimed in claim 1 wherein said allograft bone is cortical bone.

4. A bone screw as claimed in claim 1 wherein said tapered undercut when extended to intersect a longitudinal center axis of said shank forms an angle ranging from about 20° to about 30°.

5. A sterile bone screw constructed of allograft bone comprising: a cylindrical shank with a portion provided with a thread of a given pitch running along a portion of its length, another portion of said shank being unthreaded and formed with an outwardly flaring frustrum conical section having a diameter which is greater than the diameter of said threaded portion and an end surface which is transverse to the axis of said shank, said outwardly flaring section being positioned adjacent to and integrally formed with a drive head having a rectangular configuration.

6. A sterile bone screw as claimed in claim 5 wherein said screw is threaded about ½ the length of the shank.

7. A sterile bone screw as claimed in claim 5 wherein said screw is threaded over ½ the length of the shank.

8. A sterile bone screw as claimed in claim 5 wherein said screw has a thread with a height of about 0.35 mm.

9. A bone screw as claimed in claim 5 wherein said screw is threaded substantially the length of the shank.

10. A sterile bone screw as claimed in claim 5 wherein said bone screw is constructed of cortical allograft bone.

11. A bone screw as claimed in claim 5 wherein said allograft bone is at least partially demineralized.

12. A sterile bone screw as claimed in claim 5 wherein said screw has bone morphogenic protein added thereto.

13. A sterile bone screw as claimed in claim 5 wherein said screw drive head body defines a wedge shaped end portion.

14. A sterile bone screw as claimed in claim 13 wherein said wedge shaped end portion has a rounded tip.

15. A sterile bone screw constructed of allograft bone comprising: a cylindrical shank with a diameter of at least 2.80 mm with a portion of said shank being provided with a thread of a given pitch running along at least a portion of its length; said thread having a height ranging from 10% to 15% of said shank diameter, another portion of said shank being unthreaded and formed in an outwardly flaring conically shaped section having a diameter which is greater than the diameter of said threaded portion, said outwardly flaring conically shaped section being positioned adjacent to and integrally formed with a drive head having a rectangular body configuration provided with a wedge shaped end.

16. A sterile bone screw as claimed in claim 15 wherein said bone screw is treated with a bone morphogenic protein.

* * * * *